(12) United States Patent
Edye et al.

(10) Patent No.: US 8,999,067 B2
(45) Date of Patent: Apr. 7, 2015

(54) FRACTIONATION OF A LIGNOCELLULOSIC MATERIAL

(75) Inventors: Leslie Alan Edye, Highland Park (AU); William Orlando Sinclair Doherty, Calamvale (AU)

(73) Assignee: Queensland University of Technology, Brisbane, Queensland (AU)

( * ) Notice: Subject to any disclaimer, the term of this patent is extended or adjusted under 35 U.S.C. 154(b) by 1242 days.

(21) Appl. No.: 12/526,474

(22) PCT Filed: Feb. 7, 2008

(86) PCT No.: PCT/AU2008/000153
§ 371 (c)(1), (2), (4) Date: Apr. 15, 2010

(87) PCT Pub. No.: WO2008/095252
PCT Pub. Date: Aug. 14, 2008

(65) Prior Publication Data
US 2010/0196967 A1   Aug. 5, 2010

(30) Foreign Application Priority Data
Feb. 7, 2007   (AU) ............................... 2007900603

(51) Int. Cl.
| | | |
|---|---|---|
| C08B 1/00 | (2006.01) |
| C12P 19/02 | (2006.01) |
| C12P 7/10 | (2006.01) |
| C12P 19/04 | (2006.01) |
| C13K 1/02 | (2006.01) |
| D21C 11/00 | (2006.01) |
| D21C 5/00 | (2006.01) |

(52) U.S. Cl.
CPC . *C12P 7/10* (2013.01); *C12P 19/04* (2013.01); *C13K 1/02* (2013.01); *D21C 5/005* (2013.01); *D21C 11/0007* (2013.01); *Y02E 50/16* (2013.01)

(58) Field of Classification Search
CPC .................................................. D21C 11/0007
See application file for complete search history.

(56) References Cited

U.S. PATENT DOCUMENTS

| 4,946,946 A * | 8/1990 | Fields et al. ................... 530/500 |
| 6,808,557 B2 | 10/2004 | Holbrey et al. ............ 106/200.2 |
| 6,824,599 B2 | 11/2004 | Swatloski et al. .......... 106/200.2 |
| 2007/0161095 A1 | 7/2007 | Gurin .......................... 424/94.6 |

FOREIGN PATENT DOCUMENTS

| WO | WO 03/029329 | 4/2003 |
| WO | WO 2005/017001 | 2/2005 |
| WO | WO 2005/017252 | 2/2005 |
| WO | WO 2005017001 A1 * | 2/2005 |
| WO | WO 2005/118828 | 12/2005 |
| WO | WO 2006/116126 | 11/2006 |
| WO | WO 2007/111605 | 10/2007 |
| WO | WO 2008/098032 | 8/2008 |

OTHER PUBLICATIONS

Gutowski et al., Controlling the Aqueous Miscibility of Ionic Liquids: Aqueous Biphasic Systems of Water-Miscible Ionic Liquids and Water-Structuring Salts for Recycle, Metathesis, and Separations, 2003, J. Am. Chem. Soc. 125(22): 6632-6633.*
Li et al., Ionic liquid-based aqueous two-phase system, a sample pretreatment procedure prior to high-performance liquid chromatography of opium alkaloids, 2005, Journal of Chromatography B 826(1-2): 58-62.*
Zhu et al., Dissolution of cellulose with ionic liquids and its application: a mini-review, 2005, Green Chem. 8: 325-327.*
Sun et al., Hydrolysis of lignocellulosic materials for ethanol production: a review, 2002, Bioresource Technology 83(1): 1-11.*
Sun et al., Fractional extraction and structural characterization of sugarcane bagasse hemicelluloses, 2004, Carbohydrate Polymers 56(2): 195-204.*
Xiao et al., Chemical, structural, and thermal characterizations of alkali-soluble lignins and hemicelluloses, and cellulose from maize stems, rye straw, and rice straw, 2001, Polymer Degradation and Stability 74(2): 307-319.*
Supplementary European Search Report dated Feb. 10, 2012 for Application No. EP 08 70 0446.
Fort et al., "Can ionic liquids dissolve wood? Processing and analysis of lignocellulosic materials with 1-n-butyl-3-methylimidazolium chloride," *Green Chemistry*, 9:63-69, 2006.
Zhu et al., "Dissolution of cellulose with ionic liquids and its application: a mini review," *Green Chemistry*, 8:325-327, 2006.

* cited by examiner

*Primary Examiner* — Robert Yamasaki
(74) *Attorney, Agent, or Firm* — Dentons US LLP

(57) ABSTRACT

A method for fractionating a lignocellulosic material, the method comprising; contacting (2) the lignocellulosic material with an ionic liquid (3) and dissolving the lignocellulosic material therein, providing a second liquid (7) which is immiscible with the ionic liquid and is also a non-solvent for cellulose, adding the second liquid to the ionic liquid so as to form a biphasic system (6) which comprises an ionic liquid phase essentially free of lignocellulose and a second liquid phase comprising lignin in solution and cellulose as a precipitate, separating the two phases and recovering (8) the precipitated cellulose from the separated second liquid phase.

10 Claims, 1 Drawing Sheet

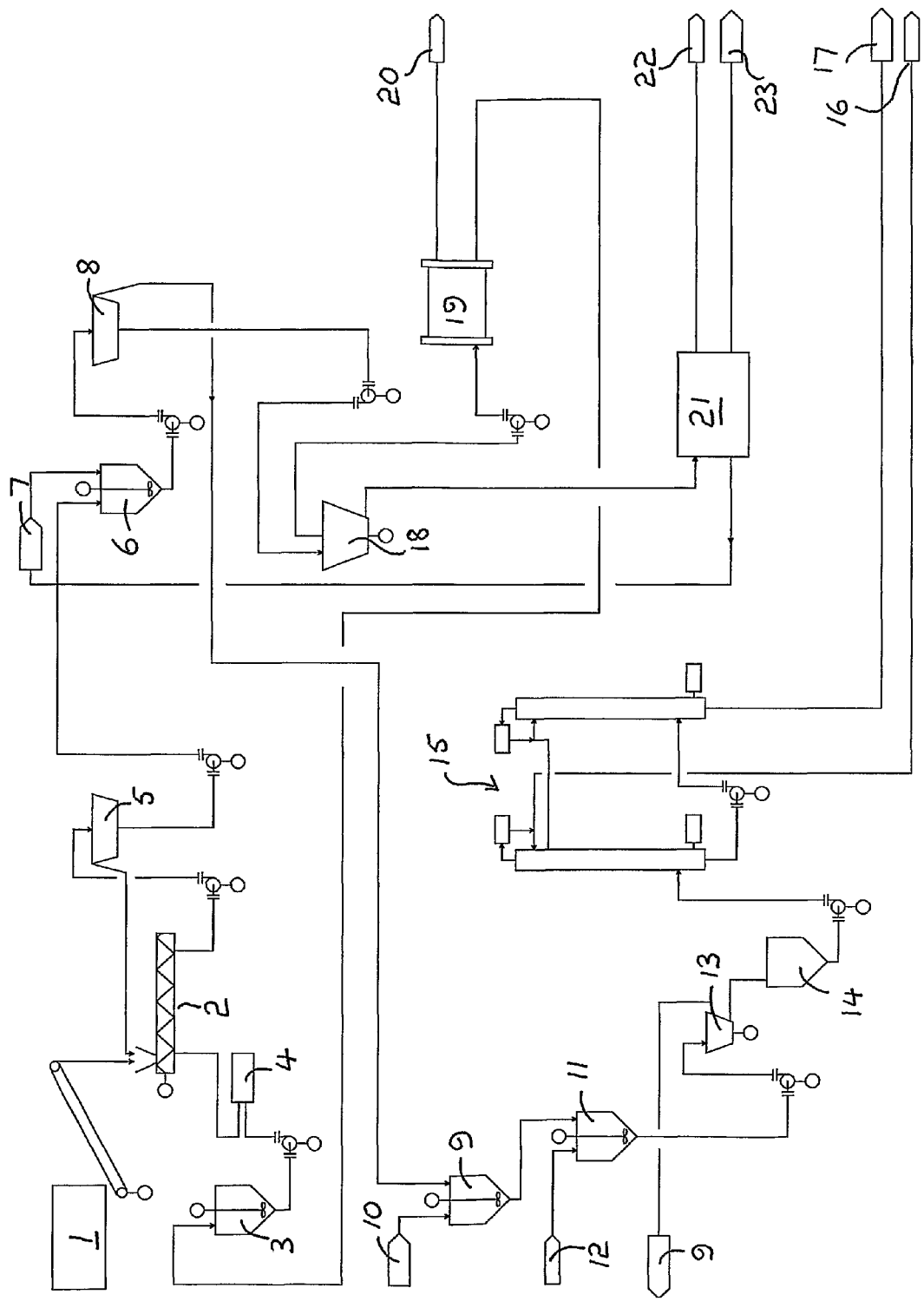

FRACTIONATION OF A LIGNOCELLULOSIC MATERIAL

The above-referenced application is a national stage application under 35 U.S.C. 371 of International Application No. PCT/AU2008/000153, filed Feb. 7, 2008, which claims priority from Australian Application No. 2007900603 filed Feb. 7, 2007.

FIELD OF THE INVENTION

The present invention relates to fractionation of a lignocellulosic material and in particular relates to separating cellulose therefrom.

BACKGROUND OF THE INVENTION

The present invention will be described with particular reference to fractionation of a lignocellulosic material to obtain cellulose in a form suitable for enzymatic hydrolysis and fermentation to ethanol. However, it will be appreciated that the fractionated products obtained by the methods of the present invention may have other end uses and no limitation is intended thereby.

Cellulose, together with lignin and hemicellulose, is found in the cell wall of plants. Plant cell wall material is also known as biomass or lignocellulose. The terms biomass and lignocellulose have the same meaning here. Cellulose is primarily used to manufacture pulp and paper products, textiles and fibres. Cellulose has been proposed as an alternative source of its component sugar glucose. Glucose may be readily fermented to ethanol which is considered a valuable biofuel. Ethanol is currently produced from hydration of ethylene from petroleum stocks or from natural starches from corn and sugar from sugar cane or beet. Starch and sugar are relatively easily hydrolysed to their component monosaccharides. However, corn and sugar are also a valuable food source and product on their own right. It would be desirable to be able to obtain ethanol from a non-food source and in particular a waste product. The use of cellulose as a source of "bioethanol" has therefore been proposed.

Hydrolysis of cellulose to glucose may be carried out chemically or enzymaticly. Chemical hydrolysis involves the use of concentrated acids such as sulphuric acid. Acid hydrolysis is economically unfavourable in view of the costs of the acids. Enzymatic hydrolysis offers a more favourable economic result, but only if the enzymes are able to be continuously recycled or used at suitably low dose rates. However the presence of lignin and hemicellulose to some extent deactivate cellulase enzymes. Thus, separation of these components from cellulose is important for an efficient and economically viable process. Furthermore, cellulose in its native state in fibrous plants is partially crystalline and this crystalline component resists enzymatic hydrolysis. Current commercial methods for fractionating lignocellulosic material such as the Kraft process either do not sufficiently separate the lignin from cellulose or produce cellulose with most of the crystalline component preserved. Cellulose sourced from these processes is thus not well suited for enzymatic degradation. A further disadvantage of these commercial processes is that they generate undesirable pollutants. Consequently there is considerable interest in obtaining an environmentally acceptable and commercially viable method of fractionating lignocellulosic materials.

Cellulose is known to be able to be dissolved in ionic liquids. Ionic liquids are organic salts which exist as liquids at relatively low temperatures. Currently, cellulose processing and chemistry relies primarily on carbon disulfide and caustic bases as dissolving solutions. The efficiency of existing methods for dissolving and derivatizing cellulose can be significantly improved by the availability of suitable solvents for refined and natural cellulose. Solutions of cellulose and ionic liquids are amenable to conventional processing techniques for the formation of cellulose threads, thin films, and beads. For example, dyes, as well as complexants for coordination and binding of metal ions, that are insoluble in water can be readily dissolved in this polar ionic liquid at high concentration. In this way, they can be integrated into a processed hydrophilic cellulose matrix to obtain materials suitable for sensing and remediation in aqueous media.

Cellulose dissolved in an ionic liquid is recovered according to the conventional polymer chemistry technique of adding a miscible non-solvent to a polymer solution. The desired cellulose polymer forms a precipitate in the single phase and can be recovered by conventional liquid/solid separation techniques. Polymers precipitated in this manner are generally contaminated with the dissolving liquid which must be separated from the precipitated material. Such separation is known to be difficult in the case of cellulose precipitated from an ionic liquid. Further, ionic liquids are quiet expensive which means that in order for a process to be commercially viable, the ionic liquid must be able to be recycled in a relatively efficient manner. However, separation of the miscible non-solvent has also proven difficult. The present inventors are unaware of any commercial process for processing cellulose that involves the use of ionic liquids.

The present invention relates to a method of fractionating a lignocellulosic material and obtaining cellulose therefrom.

BRIEF DESCRIPTION OF THE INVENTION

According to a first broad form of the invention there is provided a method for fractionating a lignocellulosic material, the method comprising; contacting the lignocellulosic material with an ionic liquid and dissolving the lignocellulosic material therein;

providing a second liquid which is immiscible with the ionic liquid and is also a non-solvent for cellulose;

adding the second liquid to the ionic liquid so as to form a biphasic system which comprises an ionic liquid phase essentially free of lignocellulose and a second liquid phase comprising lignin in solution and cellulose as a precipitate;

separating the two phases and recovering the precipitated cellulose from the separated second liquid phase.

The lignocellulosic material that may be processed by the method of the present invention may be any plant derived material containing cellulose and lignin, such as timber, logging waste, wood chips, grasses, waste agricultural material such as bagasse, corn husks, seed hulls, waste pulp and paper products, and the like.

The term "immiscible" is used in its conventional sense to refer to two liquids that are less than completely miscible, in that mixing two such liquids results in a mixture containing more than one liquid phase. It will be appreciated that some transfer of liquid may occur between the phases.

The term "biphasic system" is used to refer to a system obtained by mixing two immiscible liquids together to obtain a system having two liquid phases.

The lignocellulosic material is dissolved in an ionic liquid. The cations of the ionic liquid are preferably cyclic and correspond in structure to a formula selected from the group consisting of:

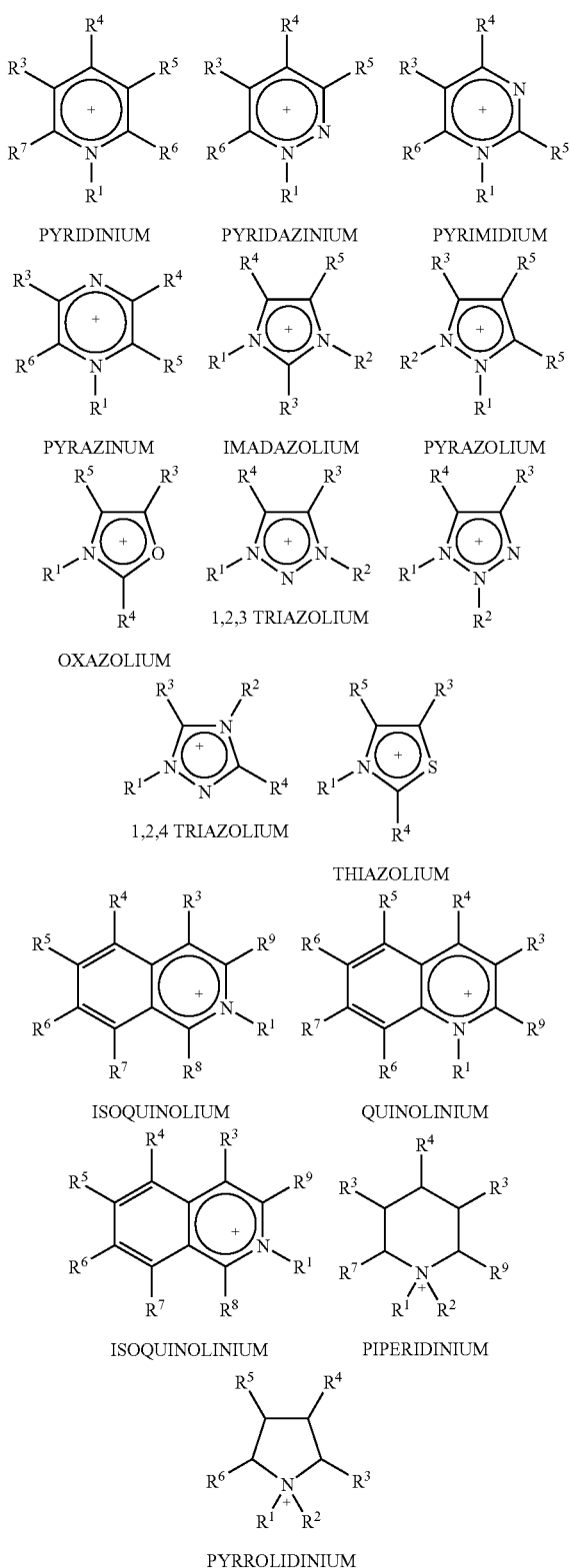

wherein $R^1$ and $R^2$ are independently a $C_1$ to $C_6$ alkyl group or a $C_1$ to $C_6$ alkoxyalkyl group and $R^3$, $R^4$, $R^5$, $R^6$, $R^7$, $R^8$ and $R^9$ when present are independently a hydrido, a $C_1$ to $C_6$ alkyl, a $C_1$ to $C_6$ alkoxyalkyl group or a $C_1$ to $C_6$ alkoxy group. In this formula alkyl groups may contain one or more double bonds, for example an allyl group.

The anions of the ionic liquid include halogens (for example chloride), pseudohalogens (for example an azide or an isocyanate), a $C_1$ to $C_6$ carboxylate or a sulfonate. Alternatively the ionic liquid may contain a binary, ternary or more complex mixture of cations which may include halogens, pseudohalogens, $C_1$ to $C_6$ carboxylates, sulfonates or arylsulfonates of the formula

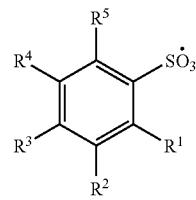

wherein $R^1$, $R^2$, $R^3$, $R^4$ and $R^5$ are independently a hydrido, a $C_1$ to $C_6$ alkyl or an aryl group. Importantly a halogen or pseudohalogen will be included in this mixture at a concentration sufficient to disrupt hydrogen bonds in the cellulose fibres and effect dissolution of cellulose.

The second liquid which is immiscible with the ionic-liquid and non-solvent for cellulose is an aqueous alkali solution such as KOH, MgOH or NaOH, an aqueous salt solution or a mixture thereof. The pH of the solution is typically within the ranges used in conventional processes to extract lignin from a lignocellulosic material. Typically solutions may have a pH from between about 8 to about 14. A preferred second liquid is a 15-25 w/v % NaOH, with 20% being especially preferred.

The alkali solution may also include a halide salt. Whilst not wishing to be bound by theory, it is believed the presence of a salt may reduce the level of ion exchange between the phases. A preferred salt is a chloride salt with sodium chloride in the range of 10 to 50 g/L being particularly preferred.

The present inventors have also unexpectedly discovered that dissolution of the lignocellulosic material may be facilitated by the presence of moisture in the material and in particular at temperatures at which water is able to undergo evaporation form the material. Whilst not wishing to be bound by theory, the present inventors believe that as the water evaporates the ionic liquid is able to move into the spaces vacated by the water thereby improving the penetration of the ionic liquid into the lignocellulosic material.

It has also been discovered that dissolution may be facilitated if the ionic solution is heated to a temperature above the glass transition temperature of the lignin. The glass transition temperature can vary depending upon the source of the lignin but is typically between about 125 to about 145° C. Preferably, the liquid is heated to at least about 120° C. and typically to between about 130 and 190° C. Preferably the ionic liquid is not heated above about 200, more preferably 190° C.

It will be appreciated that dissolution may also be facilitated by other methods in addition to or instead of heating. Such alternate methods include agitation, microwave irradiation or physical pre-treatment of the lignin such as fine or ultragrinding. One of skill in the art will also appreciate that dissolution may also be dependent upon the source of the lignin The water may be inherent in the material, for example bagasse has a typically moisture content of between about 40 to about 70% or may be added to or absorbed by the material.

The biphasic system may be separated by any suitable phase separation technique. After separation, the precipitated cellulose is recovered from the second liquid phase. This separation may also be conducted by suitable methods known in the art such as filtration, centrifugation or the like. Preferably prior to separation the aqueous phase is agitated so as to disperse the precipitated cellulose therein.

The inventors have surprisingly and unexpectedly observed that the ionic liquid residue is in a relatively pure form and may be reused with little or no subsequent treatment.

The present invention may provide cellulose essentially free of hemicellulose contamination. Further it has been reported that enzymatic hydrolysis of cellulose reprecipitated from ionic solutions (using miscible cellulose non solvents) is amorphous and enzymatic hydrolysis thereof occurs at a faster rate than untreated cellulose. The method of the present invention may therefore provide cellulose in an amorphous form which may be readily susceptible to enzymatic hydrolysis.

A particularly preferred downstream processing of cellulose isolated by the method of the present invention is in the production of ethanol.

According to a further broad form of the invention there is provided a method for producing ethanol, the method comprising:
contacting a lignocellulosic material with an ionic liquid and dissolving the lignocellulosic material therein;
providing a second liquid which is immiscible with the ionic liquid and is also a non-solvent for cellulose;
adding the second liquid to the ionic liquid so as to form a biphasic system which comprises an ionic liquid phase essentially free of lignocellulose and a second liquid phase comprising lignin in solution and cellulose as a precipitate;
separating the two phases;
recovering the precipitated cellulose from the separated second liquid phase and
subjecting the recovered cellulose to hydrolysis and fermentation.

Methods of hydrolysis and fermentation of cellulose to produce ethanol are known to those of skill in the art and need not be described in detail. The hydrolysis and fermentation steps may be carried out sequentially simultaneously. The simultaneous hydrolysis and fermentation is known in the art as simultaneous saccharification and fermentation or SSF.

In a preferred method of the invention, the second liquid phase after removal of the cellulose is further treated so as to extract lignin and optionally hemicellulose therefrom. Techniques for isolating lignin from caustic solutions are known. Typically the caustic solution containing lignin is acidified which causes the lignin to precipitate where it can be isolated by conventional solid separation techniques. Acidification may be conducted by the addition of carbon dioxide gas or the addition of a mineral acid. The lignin may then be recovered according to known solid/liquid separation techniques.

The hemicellulose remains in the acidified solution and can be recovered by know processes that may include but are not limited to cooling, membrane filtration (ultra filtration or reverse osmosis) and chromatography. Alternatively, the hemicellulose may be not be recovered, in which case the aqueous solution can then be treated using processes practised in soda pulping mills (for example wet air oxidation or direct alkali recovery) to obtain an aqueous solution fit for reuse.

It is known to regenerate cellulose from an ionic liquid solution by the addition of a non-solvent for cellulose that is miscible with the ionic liquid such that the cellulose precipitates. The ionic liquids may be recovered by methods such as ionic exchange, reverse osmosis and salting out. Cellulose regenerated in this manner is amorphous rather than crystalline which makes it more suitable for certain downstream processing. However, recovery of the ionic liquid from the miscible non-solvent is difficult and costly.

According to a further broad form of the invention, there is provided a method for regenerating cellulose, the method comprising contacting cellulose with an ionic liquid so as to dissolve the cellulose therein;
providing a second liquid which is immiscible with the ionic liquid and is also a non-solvent for cellulose;
adding the second liquid to the ionic liquid so as to form a biphasic system which comprises an ionic liquid phase essentially free of lignocellulose and a second liquid phase comprising lignin in solution cellulose as a precipitate;
separating the two phases and
recovering the precipitated cellulose from the separated second liquid phase.

BRIEF DESCRIPTION OF THE FIGURE

FIG. 1 illustrates a flow chart representing a preferred method of the present invention.

Biomass is conveyed from a biomass storage bunker (1) to a pretreatment reactor (2) where it is mixed with an ionic liquid. The ionic liquid is stored in a storage tank (3) and passes through a feed heater (4) on the way to the pretreatment reactor (2) in which the biomass dissolves in the ionic liquid. The ionic liquid is heated to about 170° C. After dissolution of the biomass, the ionic liquid/biomass solution passes through a filter (5) to remove any undissolved matter and is delivered to a cellulose precipitation tank (6). Caustic soda (7) is added to the cellulose precipitation tank (6) to produce a biphasic system. Cellulose precipitates and the lignin and hemicelluloses migrate to the caustic phase. The biphasic mixture passes through a cellulose filter (8).

The solids obtained from the cellulose filter are further processed in a hydrolytic reactor (9) in which the acid or enzymes (10) are added such that the cellulose is subjected to enzymatic or acid hydrolysis. The hydrolysis products are then subjected to fermentation (11) by the addition of yeast (12). After fermentation, solids (9) are removed by centrifugal solids separation (13), followed by storage (14) and distillation (15) produce ethanol (16) and aqueous residue (17).

The filtrate from the cellulose filter (8) is subjected to centrifugation (18) to separate the ionic liquid and caustic phases. The ionic liquid is reconcentrated (19) to remove water (20) and recycled to the ionic liquid storage tank (3). The caustic phase that contains lignin and hemicellulose is passed to a further reactor (21) in which the pH is lowered until lignin precipitates and is separated (22). The remaining solution contains dissolved hemicelluloses. Hemicellulose is removed (23) by membrane filtration. The caustic is reconcentrated and recycled to the caustic storage tank (5).

EXAMPLES

By way of Example only, the present invention will be illustrated with reference to the following non-limiting examples.

Example 1

Dissolution of Wet and Dry Bagasse in 1-butyl-3-methylimidazolium Chloride 0.0982 g of normal bagasse (at typical or intrinsic moisture level of 58.48% mass water) was added to 6.9440 g 1-butyl-3-methylimidazolium chloride and 0.0411 g of dried bagasse was added to 6.8905 g of 1-butyl-3-methylimidazolium chloride in glass tubes of identical dimensions so that both tubes contained the same dry bagasse:solvent (1-butyl-3-methylimidazolium chloride) ratios. The contents of both tubes were stirred at the same rate and immersed in an oil bath heated to 175° C. to 178° C. Qualitative observations of the dissolution process are reported in the following table.

| Time (minutes) | Normal bagasse | Dried bagasse |
|---|---|---|
| 2 | Moisture condensation on neck of tube Darkening of liquid | No change |
| 10 | Small particles all dissolved, only larger fibres (>0.3 cm) remain) | Some darkening of liquid, small particles remain undissolved |
| 15 | Large fibres are noticeably swollen | Some small particles still remain |
| 20 | Only ca. 10% of larger fibres remain visible | Small particles dissolved, some larger fibres beginning to swell |
| 25 | Bagasse is completely dissolved | ca. 80% of larger fibres remain but are noticeably swollen |
| 35 | | Some larger fibres remain visible |
| 42 | | Bagasse almost completely dissolved. Only 3 or 4 recalcitrant fibres remain visible |

Example 2

Dissolution of Lignocellulose and Recovery of Cellulose from 1-butyl-3-methylimidazolium Chloride 2.72 g of normal bagasse (at typical moisture level of 58.48% mass water) was added to 43.18 g of 1-butyl-3-methylimidazolium chloride. The mixture was stirred and heated to 170° C. After ca. 30 minutes the bagasse was completely dissolved. The bagasse in ionic liquid solution was cooled to ca. 100° C. and an aqueous NaOH solution (20 mL of 114 g/L) was added. The resulting mixture contained two liquid phases, namely an ionic liquid phase and an aqueous phase. Upon shaking the aqueous phase became cloudy and dark coloured and the ionic liquid phase became lighter coloured such that it resembled the ionic liquid starting material rather than the bagasse in ionic liquid solution. In addition a precipitate formed in the aqueous phase at the boundary of the two liquid phases. This precipitate could be suspended evenly in the aqueous phase by gentle stirring. The two liquid phases were separated by decanting.

$^1$H NMR of the ionic liquid phase indicated that it contained 1-butyl-3-methylimidazolium chloride (and also some hydroxide) but no measurable bagasse (lignocellulosic) residue. The recovered ionic liquid (44.36 g) contained some water but was considered to be free of residual bagasse since no further precipitate was obtained when more water was added to a portion of this ionic liquid. Furthermore, the recovered ionic liquid could be reused to dissolve bagasse.

The precipitate (0.54 g) was separated from the aqueous phase by centrifugation and by analysis was found to comprise cellulose with no detectable lignin or hemicellulose. The lignin which remained in solution in the aqueous NaOH was precipitated (to yield 0.22 g) by the addition of mineral acid (e.g. $H_2SO_4$ or HCl, but bubbling $CO_2$ would have a similar acidifying effect).

Example 3

Biphasic Ionic Liquid/Aqueous Hydroxide Systems with and without a Halide Salt 1 mL of aqueous solutions containing sodium hydroxide or sodium hydroxide and sodium chloride mixtures were added to vials containing approximately 0.7 g of 1-butyl-3-methylimidazolium chloride. On addition, the vials were either shaken or not disturbed and then observed over a period of up to 70 minutes. Qualitative observations are reported in the following table. Concentrations are shown in weight/volume percentages.

| Aqueous solution | treatment | observation |
|---|---|---|
| 10% NaOH + 10% NaCl | Shaken | Slow formation of a biphasic system with a hazy interface after 70 minutes |
| 10% NaOH + 10% NaCl | Not disturbed | Fast formation of biphasic system with sharp interface in 5 minutes |
| 5% NaOH + 5% NaCl | Shaken | No formation of a biphasic system after 70 minutes |
| 5% NaOH + 5% NaCl | Not disturbed | Slow formation of a biphasic system with no sharp interface after 25 minutes and unstable |
| 20% NaOH | Shaken | Formation of biphasic system with sharp interface in less than 1 minute* |
| 20% NaOH | Not disturbed | Fast formation of biphasic system with sharp interface in less than 2 minute |

*Both layers of the biphasic system were cloudy after 1 minute but became clear after 2.5 minutes.

In all cases where a biphasic system formed the volume of the 1-butyl-3-methylimidazolium chloride layer was larger that the original volume of the ionic liquid. Analysis of both layers by infra-red spectroscopy and ion chromatography confirmed that while water migrated into the 1-butyl-3-methylimidazolium chloride layer, the sodium salts remained in the aqueous layer and the ionic liquid did not permeate the aqueous layer. Consequently the final concentrations of salts in the aqueous layer were higher than at addition.

This example shows that stable biphasic systems can be obtained with varying levels of NaOH and further that the biphasic system tolerates the presence of a halide salt.

Example 4

Dissolution of Lignocellulose in 1-ethyl-3-methylimidazolium Acetate 0.199 g of dried and milled bagasse (2 mm sieved and at moisture level of 6% mass water) was added to 15.494 g of 1-ethyl-3-methylimidazolium acetate. The mixture was stirred and heated to 170° C. After ca. 50 minutes the bagasse was completely dissolved.

Example 5

Dissolution of Lignocellulose and Recovery of Cellulose from 1-butyl-3-methylimidazolium Chloride at a High Solute to Solvent Ratio 60.0 g of dried and milled bagasse (1 mm sieved and at moisture level of 6% mass water) was added to 400.0 g of 1-butyl-3-methylimidazolium chloride. The mixture was stirred and heated to 170° C. After ca. 3 hours the bagasse was completely dissolved. The bagasse in ionic liquid solution was divided into two approximately equal portions with one portion being set aside for other purposes. The remaining portion (1989.85 g) was cooled to ca. 100° C. and an aqueous NaOH solution (290.9 g of 20% w/v) was added. The mixture was stirred then allowed to settle into two liquid phases, namely an ionic liquid phase (top layer) and an aqueous phase (bottom layer). The aqueous phase contained a precipitate which concentrated at the interface with the ionic liquid layer. The aqueous layer proved difficult to filter under laboratory conditions so a portion was filtered and dried to yield 4.50 g of cellulosic material.

Example 6

Determination of the Minimum Temperature for Significant Dissolution of Lignocellulose in 1-butyl-3-methylimidazolium Chloride 45.24 g of dried and milled bagasse (1 mm sieved and at moisture level of 6% mass water) was added to 445.5 g of 1-butyl-3-methylimidazolium chloride. The mixture was stirred and heated to 90° C. for 1 hour. The temperature was then increased to 10° C. steps and held at each temperature for up to 20 minutes. Attenuated total reflectance infra-red spectroscopy was used to monitor the onset of dissolution. Specifically the lignin absorption at the wave number of 1510 $cm^{-1}$ was continuously monitored to determine the point at which measurable amounts of lignin dissolved in the ionic liquid. The temperature at the onset of lignin dissolution was 122° C. The temperature at 2 hours was 130° C. Whilst not wishing to be bound by theory, the present inventors believe that the ionic liquid has two possible effects on the lignin, namely breaking carbon to oxygen bonds and acting as a plasticiser. Both of these lower the glass transition temperature of the lignin (which would otherwise be around 135° C. but is reported in literature as being between 120° C. and 140° C.). This dissolution experiment confirmed that heating to about the glass transition of lignin in the reaction system facilitated dissolution.

Example 7

Enzymic Hydrolysis and Fermentation of Cellulosic Material Recovered from Lignocellulose Dissolved into 1-butyl-3-methylimidazolium Chloride 0.27 g of dried yeast and 0.1 mL of a cellulolytic enzyme cocktail was added to vials containing ca. 1.0 g of a cellulosic material recovered under conditions described in example D. The mixture was weighed and placed in a shaker incubator and held at a temperature of 37° C. Similarly vials were prepared containing 1 g of Solka floc, Avicel or glucose. Solka Floc and Avicel are commercially available cellulose materials. Avicel is a microcrystalline cellulose.

The vials containing glucose were actively fermenting after 15 minutes. The vials containing the recovered cellulosic material or Solka floc were actively fermenting after 75 minutes. The vials containing Avicel appeared to be beginning to ferment after 75 minutes. After 18.5 hours the vials were re-weighed and the extent of ethanol production determined by the weight loss resulting from concurrent carbon dioxide production. Weight loss values were corrected for water evaporation by similar measurements on a vial containing water, yeast and enzyme only. The results are reported in the following table as percentages of theoretical conversion of the fermentables added to each vial and demonstrate that the material recovered from ionic liquid dissolution processes undergo enzymic hydrolysis more rapidly than commercial cellulose preparations and are fermentable to ethanol by conventional yeasts.

| Substrate | Conversion to ethanol (% theoretical yield) |
| --- | --- |
| Solka floc | 43.6 |
| Avicel | 23.6 |
| Glucose | 103.0 |
| Recovered cellulosic material | 72.3 |

It may be seen that the method of the present invention allows cellulose to be separated from a lignocellulosic material to provide cellulose in a form that may be efficiently hydrolysed and fermented. The method uses an ionic liquid that may be easily recycled without requiring the difficult and costly steps of separating an ionic liquid from a miscible solvent as per the prior art.

In the specification and the claims the term "comprising" shall be understood to have a broad meaning similar to the term "including" and will be understood to imply the inclusion of a stated integer or step or group of integers or steps but not the exclusion of any other integer or step or group of integers or steps. This definition also applies to variations on the term "comprising" such as "comprise" and "comprises".

It will be appreciated that various changes and modifications may be made to the invention as described and claimed herein without departing from the spirit and scope thereof.

The invention claimed is:

1. A method for fractionating a lignocellulosic material, the method comprising:
   contacting the lignocellulosic material with an ionic liquid and dissolving the lignocellulosic material therein;
   providing a second liquid which is immiscible with the ionic liquid and is also a non-solvent for cellulose, wherein the second liquid is an aqueous hydroxide solution;
   adding the second liquid to the ionic liquid so as to form a biphasic system which comprises an ionic liquid phase essentially free of lignocellulose and a second liquid phase comprising lignin in solution and cellulose as a precipitate;
   separating the two phases;
   recovering the precipitated cellulose from the separated second liquid phase;
   decreasing the pH of the separated second liquid phase until the lignin precipitates therefrom; and
   recovering the precipitated lignin.

2. The method of claim 1, wherein the hydroxide is sodium hydroxide.

3. The method of claim 1, wherein the ionic liquid is heated to a temperature between 120 to about 190° C.

4. The method of claim 1, further comprising the step of recovering hemicellulose from the separated second liquid phase after recovery of the lignin.

5. The method of claim 1, wherein the lignocellulosic material comprises at least some water.

6. The method of claim 5, wherein the lignocellulosic material comprises up to about 70% water.

7. The method of claim 1, wherein the lignocellulosic material comprises bagasse.

8. The method of claim 1, further comprising recycling the ionic liquid phase after separating the two phases; and contacting fresh lignocellulosic material with the recycled ionic liquid phase.

9. The method of claim 1, wherein the aqueous hydroxide solution is an aqueous sodium hydroxide solution between about 10 to about 25 w/v%.

10. A method for producing ethanol, the method comprising:

contacting a lignocellulosic material with an ionic liquid and dissolving the lignocellulosic material therein;

providing a second liquid which is immiscible with the ionic liquid and is also a non-solvent for cellulose;

adding the second liquid to the ionic liquid so as to form a biphasic system which comprises an ionic liquid phase essentially free of lignocellulose and a second liquid phase comprising lignin in solution and cellulose as a precipitate, wherein the second liquid is an aqueous hydroxide solution separating the two phases;

recovering the precipitated cellulose from the separated second liquid phase;

subjecting the recovered cellulose to hydrolysis and fermentation, decreasing the pH of the separated second liquid phase until the lignin precipitates therefrom; and recovering the precipitated lignin.

* * * * *